(12) United States Patent
Denk

(10) Patent No.: US 9,656,082 B2
(45) Date of Patent: May 23, 2017

(54) ACCELERATION SENSORS FOR RECORDING OF TRIGGERED RESPIRATORY SIGNALS IN NEUROSTIMULATORS

(71) Applicant: MED-EL Elektromedizinische Geraete GmbH, Innsbruck (AT)

(72) Inventor: Christian Denk, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 15/340,007

(22) Filed: Nov. 1, 2016

(65) Prior Publication Data

US 2017/0043168 A1    Feb. 16, 2017

Related U.S. Application Data

(62) Division of application No. 14/677,018, filed on Apr. 2, 2015.

(Continued)

(51) Int. Cl.
*A61N 1/36* (2006.01)
*A61B 5/0488* (2006.01)
(Continued)

(52) U.S. Cl.
CPC ........ *A61N 1/36135* (2013.01); *A61B 5/0488* (2013.01); *A61B 5/0816* (2013.01);
(Continued)

(58) Field of Classification Search
CPC ............. A61N 1/36139; A61N 1/3601; A61N 1/0517; A61N 1/3611
See application file for complete search history.

(56) References Cited

U.S. PATENT DOCUMENTS 5,056,519 A     10/1991   Vince
5,483,969 A     1/1996    Testerman et al.
(Continued)

FOREIGN PATENT DOCUMENTS

WO     WO 96/36395     11/1996

OTHER PUBLICATIONS

International Searching Authority, Authorized Officer Lee W. Young, International Search Report and Written Opinion, PCT/US15/24018, date of mailing Jul. 2, 2015, 14 pages.

(Continued)

*Primary Examiner* — Paula J Stice
(74) *Attorney, Agent, or Firm* — Sunstein Kann Murphy & Timbers LLP

(57) ABSTRACT

A method of developing a respiration pacing signal includes detecting respiration and movement activity in an implanted patient and developing corresponding respiration and movement signals. A respiration pacing signal is synchronized with the detected respiration activity and delivered to respiration neural tissue of the implanted patient to promote breathing of the implanted patient. A plurality of respiration sensing modes are used that reflect activity of the movement signal over time to optimize system power consumption over time, including: i. an active respiration mode when the movement signal is either actively changing or remains unchanged for a brief period less than some reduced activity period, wherein the respiration signal is measured continuously, and ii. a plurality of reduced activity respiration modes when the movement signal has remained unchanged for the reduced activity period, wherein the respiration signal is measured only during a limited respiration sampling period.

11 Claims, 4 Drawing Sheets

Related U.S. Application Data

(60) Provisional application No. 61/975,066, filed on Apr. 4, 2014.

(51) Int. Cl.
    *A61B 5/08*     (2006.01)
    *A61B 5/113*     (2006.01)
    *A61B 5/00*     (2006.01)

(52) U.S. Cl.
    CPC ............ *A61B 5/113* (2013.01); *A61B 5/4836* (2013.01); *A61B 5/686* (2013.01); *A61N 1/3601* (2013.01); *A61N 1/3611* (2013.01)

(56) References Cited

U.S. PATENT DOCUMENTS

| | | |
|---|---|---|
| 5,524,632 A | 6/1996 | Stein et al. |
| 5,800,470 A | 9/1998 | Stein et al. |
| 8,050,766 B2 | 11/2011 | Zealear |
| 8,136,532 B2 | 3/2012 | Lindenthaler et al. |
| 2005/0060001 A1 | 3/2005 | Singhal |
| 2005/0240087 A1 | 10/2005 | Keenan et al. |
| 2008/0027502 A1 | 1/2008 | Ransom |
| 2008/0103545 A1 | 5/2008 | Bolea |
| 2008/0208280 A1 | 8/2008 | Lindenthaler et al. |
| 2008/0215106 A1 | 9/2008 | Lee et al. |
| 2009/0030481 A1 | 1/2009 | Lindenthaler |
| 2011/0201969 A1 | 8/2011 | Hatlestad et al. |
| 2011/0264164 A1* | 10/2011 | Christopherson .... A61B 5/0803 607/42 |
| 2012/0150255 A1 | 6/2012 | Lindenthaler et al. |
| 2013/0310699 A1 | 11/2013 | Hart et al. |

OTHER PUBLICATIONS

International Searching Authority, Officer Lee W. Young, International Search Report and the Written Opinion, PCT/US 15/23997, date of mailing Jul. 10, 2015, 12 pages.

\* cited by examiner

ACCELERATION SENSORS FOR RECORDING OF TRIGGERED RESPIRATORY SIGNALS IN NEUROSTIMULATORS

This application is a divisional application of co-pending U.S. patent application Ser. No. 14/677,018, filed Apr. 2, 2015, which in turn claims priority from U.S. Provisional Patent Application 61/975,066, filed Apr. 4, 2014, both of which are incorporated herein by reference in their entireties.

TECHNICAL FIELD

The present invention relates to respiration implant systems such as implantable respiration pacing systems and sleep apnea treatment systems.

BACKGROUND ART

The larynx is located in the neck and is involved in breathing, producing sound (speech), and protecting the trachea from aspiration of food and water. FIG. 1A shows a coronal section view and FIG. 1B shows a transverse section view of the anatomy of a human larynx including the epiglottis 101, thyroid cartilage 102, vocal folds 103, cricothyroid muscle 104, arytenoid cartilage 105, posterior cricoarytenoid muscle (PCAM) 106, vocalis muscle 107, cricoid cartilage 108, recurrent laryngeal nerve (RLN) 109, transverse arytenoid muscle 110, oblique arytenoid muscle 111, superior laryngeal nerve 112, and hyoid bone 113.

The nerves and muscles of the larynx abduct (open) the vocal folds 103 during the inspiration phase of breathing to allow air to enter the lungs. And the nerves and muscles of the larynx adduct (close) the vocal folds 103 during the expiration phase of breathing to produce voiced sound. At rest, respiration frequency typically varies from 12 to 25 breaths per minute. So, for example, 20 breaths per minute result in a 3 second breath duration, with 1.5 sec inspiration, and 1.5 sec exhalation phase (assuming a 50/50 ratio). The breathing frequency changes depending on the physical activity.

Unilateral and bilateral injuries or ruptures of the recurrent laryngeal nerve (RLN) 109 initially result in a temporal partial paralysis of the supported muscles in the larynx (and the hypolarynx). A bilateral disruption of the RLN 109 causes a loss of the abductor function of both posterior cricoarytenoid muscles (PCAM) 106 with acute asphyxia and life-threatening conditions. This serious situation usually requires surgical treatment of the bilateral vocal cord paralysis such as cordotomy or arytenoidectomy, which subsequently restrict the voice and puts at risk the physiologic airway protection.

Another more recent treatment approach to RLN injuries uses a respiration implant that electrically stimulates (paces) the PCAM 106 during inspiration to abduct (open) the vocal folds 103. During expiration, the vocal folds 103 relax (close) to facilitate voicing. In first generation respiration implant systems, the patient can vary the pacing/respiration frequency (breaths per minute) according to his physical load (at rest, normal walking, stairs, etc.) by manually switching the stimulation frequency of the pacer device, the assumption being that the human body may adapt to the artificial externally applied respiration frequency—within some locking-range. Thus the patient and the respiration pacemaker can be described as free running oscillators at almost the same frequency, but without phase-matching (no phase-locking). Sometimes both systems will be in phase, but other times the systems will be out of phase and thus the benefit for the patient will be reduced.

More recent second generation respiration implants generate a stimulation trigger signal to synchronize the timing of the respiration pacemaker to the respiration phase or cycle (inspiration or expiration) of the patient. The stimulation trigger signal defines a specific time point during the respiration cycle to initiate stimulation of the target neural tissue. The time point may specifically be the start or end of the inspiratory or expiratory phase of breathing, or any other defined time point. To detect the desired time point, several types of respiration sensors have been investigated to generate a respiration sensing signal that varies within each breathing cycle. These include, for example, various microphones, accelerometer sensors, and pressure sensors (positioned in the pleura gap). Electromyogram (EMG) measurements also are under investigation for use in developing a stimulation trigger signal.

Besides laryngeal pacemakers for RLN injuries, there also are respiration implant neurostimulators that electrically stimulate the hypoglossal nerve that innervates the root of the tongue for treatment of sleep apnea. These sleep apnea treatment systems use a respiration sensor that is implemented to trigger on the inhaling phase of breathing, for example, using a bioimpedance measurement or a pressure sensor in the pleural gap.

SUMMARY

Embodiments of the present invention are directed to a method of developing a respiration pacing signal in an implanted patient with impaired breathing. Respiration and movement activity are detected in the implanted patient, and corresponding respiration and movement signals are developed. A pacing processor follows a series of computer instructions fixed on a non-transitory computer readable medium to receive the respiration signal and the movement signal and generate a respiration pacing signal synchronized with the detected respiration activity. The respiration pacing signal then is delivered from the pacing processor with a stimulating electrode to respiration neural tissue of the implanted patient to promote breathing of the implanted patient. Using the pacing processor includes using a plurality of respiration sensing modes that reflect activity of the movement signal over time to optimize system power consumption over time, wherein the plurality of respiration sensing modes includes: i. an active respiration mode when the movement signal is either actively changing or remains unchanged for a brief period less than some reduced activity period, wherein the respiration signal is measured continuously, and ii. a plurality of reduced activity respiration modes when the movement signal has remained unchanged for the reduced activity period, wherein the respiration signal is measured only during a limited respiration sampling period.

In further specific such embodiments, the plurality of reduced activity respiration modes may include an initial reduced activity respiration mode during which the movement signal has remained unchanged for an initial reduced activity period and in which the respiration signal is measured only during a limited respiration sampling period occurring around each expected breathing phase, and/or an extended reduced activity respiration mode during which the movement signal has remained unchanged for an extended reduced activity period and in which the respiration signal is measured only during a limited respiration sampling period occurring between each third to tenth breath, and/or a prolonged inactive respiration mode during which the movement signal has remained unchanged for a prolonged inactive period and in which the respiration signal is measured only once during a limited respiration sampling period occurring at the beginning of the prolonged inactive respiration mode.

The movement signal may be filtered in the plurality of reduced activity respiration modes to develop a respiratory signal representing rib cage movement. Detecting the respiration signal may include detecting an onset of inspiratory phase in the implanted patient. Detecting the respiration signal may include using a three-axis accelerometer and/or an electromyographic sensor implanted in the parasternal muscle of the implanted patient, and/or an intramuscular pressure sensor implanted in the parasternal muscle of the implanted patient.

The stimulating electrode may deliver the respiration pacing signal to the posterior cricoarytenoid muscle in the larynx, and/or to the hypoglossal nerve or the internal superior laryngeal nerve (iSLN).

Embodiments of the present invention are directed to a method of developing a respiration pacing signal in an implanted patient with impaired breathing. Respiration and movement activity are detected in the implanted patient, and corresponding respiration and movement signals are developed. A pacing processor follows a series of computer instructions fixed on a non-transitory computer readable medium to receive the respiration signal and the movement signal and generate a respiration pacing signal synchronized with the detected respiration activity and comprising a sequence of stimulation pulses at a given pulse rate, pulse width, and pulse amplitude. The respiration pacing signal then is delivered from the pacing processor with a stimulating electrode to respiration neural tissue of the implanted patient to promote breathing of the implanted patient. Using the pacing processor includes determining breathing effort of the implanted patient from the respiration signal and the movement signal and controlling pulse rate, pulse width, and pulse amplitude of the respiration pacing signal, and using the pacing processor also includes using a plurality of reduced activity modes when the movement signal has remained unchanged for the reduced activity period, wherein the respiration signal is measured only during a limited respiration sampling period.

In further such specific embodiments, determining breathing effort may specifically include accounting for thoracic movement based on the respiration signal and the movement signal, and/or detecting onset of inspiratory breathing effort in the implanted patient. The movement signal may be filtered in the reduced activity respiration mode to develop a respiratory signal representing rib cage movement. Detecting the respiration signal may include using a three-axis accelerometer, and/or an electromyographic sensor implanted in the parasternal muscle of the implanted patient, and/or an intramuscular pressure sensor implanted in the parasternal muscle of the implanted patient.

The stimulating electrode may deliver the respiration pacing signal to the larynx, and/or the hypoglossal nerve or the internal superior laryngeal nerve (iSLN).

DETAILED DESCRIPTION

Various embodiments of the present invention are directed to improved respiration implants that use a respiration sensor to detect respiration activity in the patient with impaired breathing, together with a three-axis acceleration sensor as a movement/position sensor to develop a breathing stimulus that is triggered on the respiration activity and uses multiple operating modes for improved power management of the implanted device to provide extended battery life. These various operating modes use the movement signal from the acceleration sensor to reduce the respiration sensor measurement time during periods of reduced patient activity. Such respiration implant systems include, for example, laryngeal pacemaker systems and sleep apnea treatment systems.

Figures 1A, 1B:
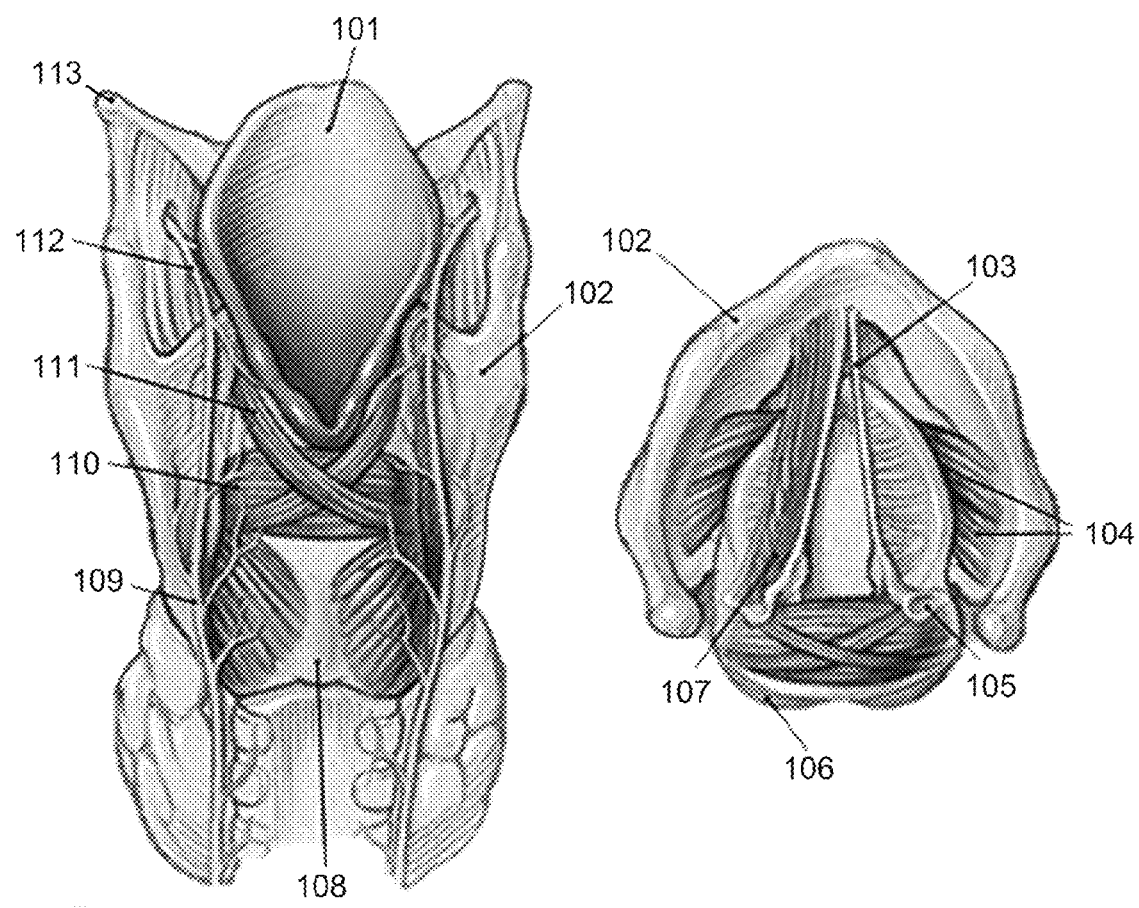
FIG. 1A shows a coronal section view and FIG. 1B shows a transverse section view of the anatomy of a human larynx.
Figure 2:
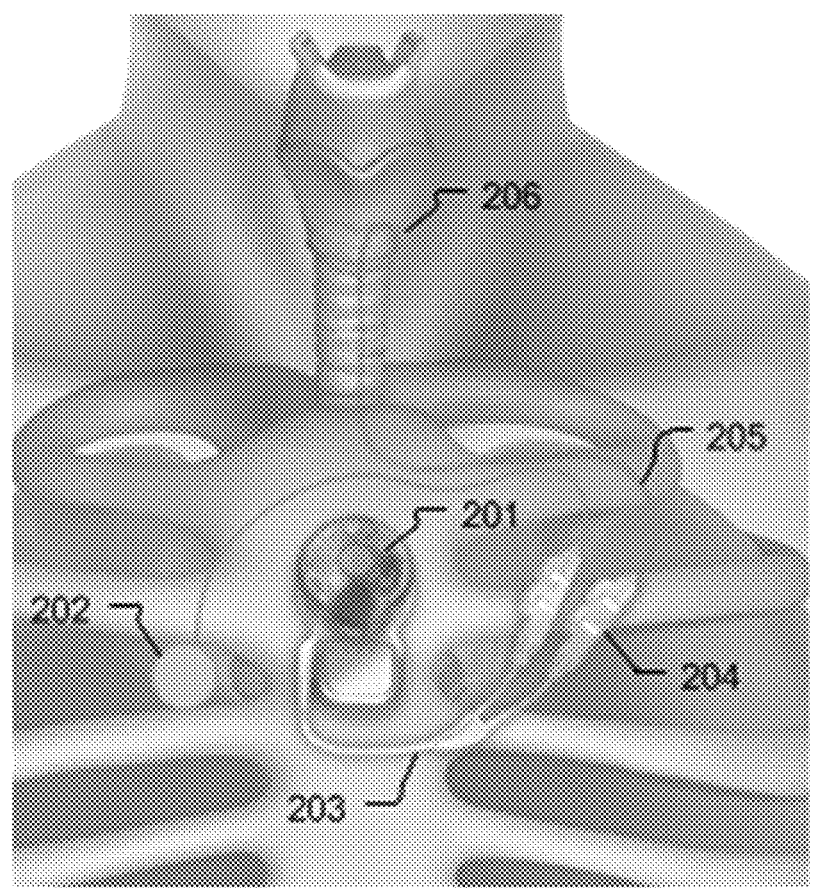
FIG. 2 shows a respiration implant system according to an embodiment of the present invention.

FIG. 2 shows one embodiment of such a respiration implant system with an implanted pacing processor 201 that receives a respiration signal from an implanted respiration sensor 202 that detects respiration activity in the implanted patient; specifically, for example, an electromyogram (EMG) sensor, pressure sensor, electroneurogram (ENG) sensor, bio-impedance sensor, temperature sensor, etc. A three-axis acceleration movement sensor is located within the housing of the pacing processor 201 and generates a movement signal that reflects the position and/or movement of the implanted patient. Based on the respiration signal and the movement signal, the pacing processor 201 generates a respiration pacing signal that is synchronized with the detected respiration activity and delivers the pacing signal via a processor lead 203 and lead interface 204 to a stimulating electrode 206 that is implanted in the target respiration neural tissue to promote breathing of the implanted patient.

The pacing processor 201 is configured to optimize system power consumption over time by using multiple respiration sensing modes that reflect physical activity over time of the patient. Specifically, different operating modes are defined based on the movement signal from the movement sensor to reduce energy consumption by reducing the measurement time of the respiration sensor 202 during periods of reduced physical activity by the patient. And the movement signal is measured at a low sampling rate in all operating modes. These operating modes are independent on the specific type of respiration sensor 202, the post signal processing and the respiration measurement time point (e.g. start or end of inspiration/expiration).

Figure 3:
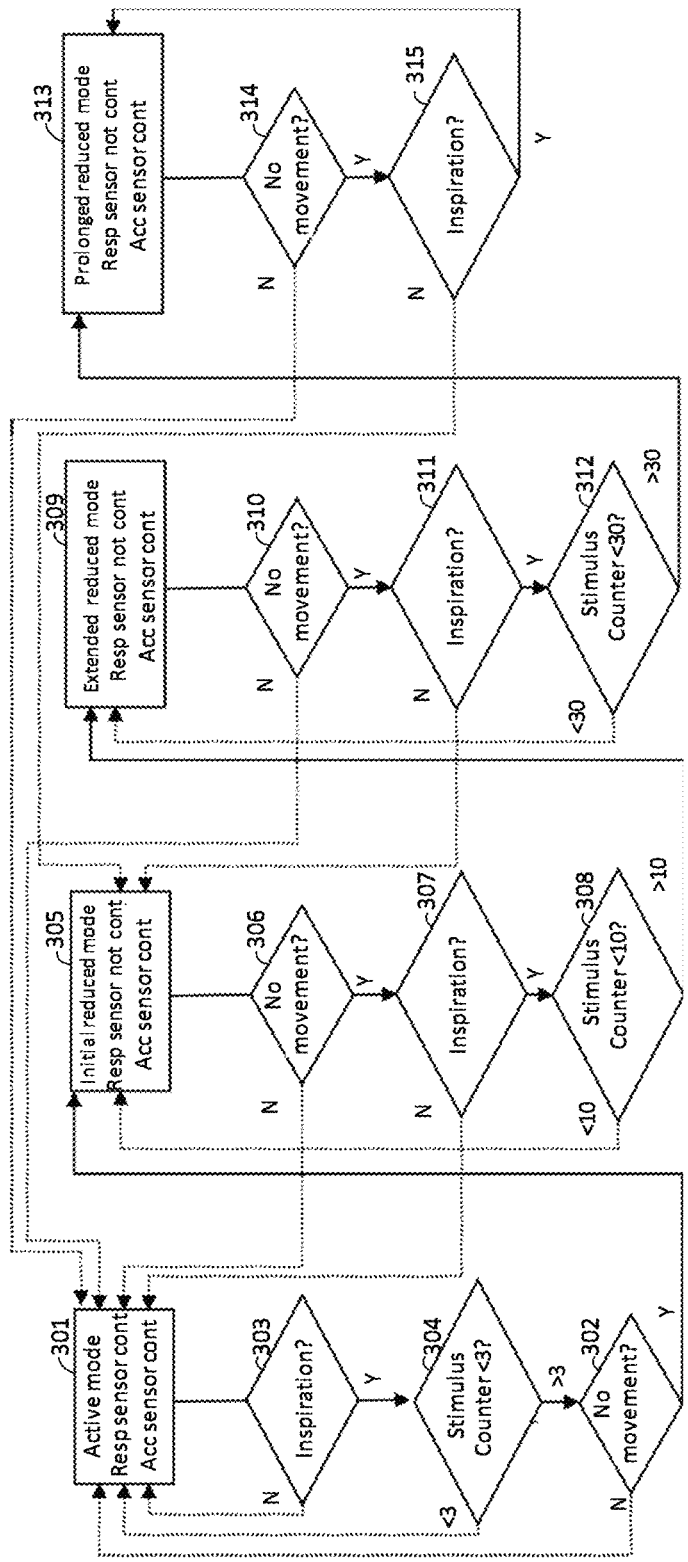
FIG. 3 shows various logical steps in the flow of power management according to one specific embodiment of the present invention.
Figure 4:
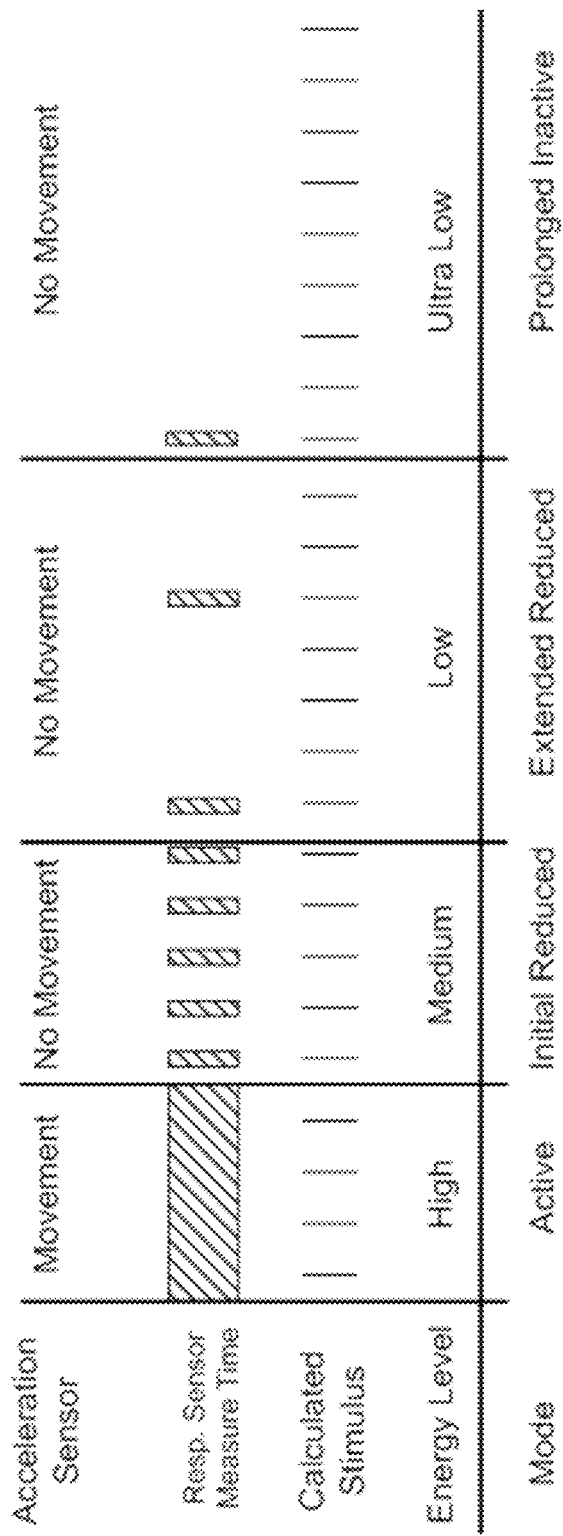
FIG. 4 summarizes in graphical form the operation of the respiration implant system in the different power management modes according to an embodiment of the present invention.

FIG. 3 shows various logical steps in the flow of power management of the respiration sensor 202 in various power management modes according to an embodiment of the present invention and FIG. 4 summarizes the different operating modes in graphical form. In all operating modes, the movement signal is measured continuously (x, y and z axes) at a relatively low sampling rate. And the stimulation timing is derived from the detected respiration activity, though as explained below, depending on the operating mode, the respiration sensor is not always active, but nevertheless respiration pacing signals are generated for each actual or expected breath.

The respiration sensing modes include a baseline active respiration mode during which the patient is engaged in physical activity and so the movement signal either is actively changing or else it remains unchanged only for a brief period that is less than some reduced activity period. And there is a reduced activity respiration mode during which the movement signal has remained unchanged for the reduced activity period and in which the respiration signal is measured only during a limited respiration sampling period. Movement is defined as a single acceleration axis or combination up to all three acceleration axes being above a given acceleration threshold. During reduced movement activity the acceleration sensor itself with proper filtering (0.1-0.5 Hz) will be able to record the respiration which correlates to the ribcage respiratory movements (acceleration derived respiration [ADR]).

While the different operating modes are explained below in greater detail, there are some general rules for when the system switches from one mode to another. As a first such general rule, if a movement signal indicates movement of the patient, the system stays in or switches to the active respiration mode (or active mode), block 301. In order to switch from one mode to the next more energy saving mode (see FIG. 4, e.g. from active to initial reduced or initial reduced to extended reduced, etc.), a characteristic mode threshold has to be fulfilled. Such a mode threshold may be a specific number of subsequently detected respiration cycles. Another mode threshold may be that a characteristic feature, e.g. the peaks or the onsets of the respiration cycles, of all (or a number of) these detected cycles relative to their expected occurrences must be within a defined percentage (e.g. 100%, 50%, 20%, 10%, 2% etc.) of the standard deviation (SD), calculated from all (or a number of) these detected cycles. The calculated SD or a percentage of it may also serve in some modes as a time window during which the respiration sensor is active (see for greater detail below). The SD may be derived from either or both of the respiration sensor and the movement sensor. The latter is possible as long as the patient motion is little or zero. If both SDs correlate within a certain value, e.g. within 20%, over a number of cycles, the SD derived from the movement sensor signal may be used and the respiration sensor may switch into a dormant mode. This has the advantage of energy saving as the operation of the movement sensor may be more energy efficient, in particular if it is an accelerometer. However, as soon as the movement sensor can no longer reliably detect a respiration cycle, the respiration sensor must be switched on again. From these measured cycles also a mean value (MV) of the characteristic feature, e.g. peak to peak distance of subsequent cycles may be calculated. This MV may serve as the basis for the calculation of subsequent expected respiratory cycles. For example, the MV*k may define the distance between the subsequent respiratory cycles, wherein k may be a real number.

During the active respiration mode (or active mode) as shown on the left side of FIG. 4, and block 301 in FIG. 3, the respiration signal from the respiration sensor 202 is measured continuously by the pacing processor 201, and the respiration pacing signal is calculated from the entire recorded respiratory sensor signal. In the active respiration mode, each respiration cycle triggers a respiration pacing stimulus. During the active mode, a respiration counter keeps track of the number of respiration cycles that occurs, block 303. The system stays in the active respiration mode whenever the movement signal from the movement sensor is active indicating movement of the patient, block 302 (and similarly, the system returns to the active respiration mode from the other operating modes whenever the movement signal from the movement sensor is active indicating movement of the patient as shown in FIG. 3, blocks 306, 310 and 314).

When the respiration counter 303 has not encountered more than a defined number of subsequent respiration cycles (e.g. more than 3 as shown in FIG. 3) or the movement signal (from movement sensor 302) has indicated movement of the patient, the pacing processor 201 remains in the active respiration mode. When the respiration counter 303 has encountered more than a defined number of subsequent respiration cycles (e.g. more than 3 as shown in FIG. 3) and the movement signal has remained unchanged for some defined active mode threshold, block 304, thus indicating no movement of the patient, the pacing processor 201 switches to an initial reduced activity respiration mode (or initial reduced mode), block 305. In this mode, the respiration sensor is only active for rather short periods which means that it measures the respiration signal only during a limited respiration sampling period around the time of the next expected breath as shown in FIG. 4 (hatched bars). This time window may be predefined in length or dynamically determined from the SD as explained above. The beginning and the end of the time window may be chosen such that it is symmetric around a characteristic feature of the expected pulses, such as the peak or the onset, e.g. derived from the MVs.

During the initial reduced mode, a respiration counter keeps track of the number of respiration cycles that occur, block 308. If no movement of the patient has been indicated by the movement sensors and none of the two sensors (respiration and movement sensor) encounter an inspiratory event that is counted in block 307, the pacing sensor 201 may switch back to active respiration mode, block 301, and recommence continuous measurement of the respiration signal. When the respiration counter 308 has encountered more than the above mentioned number of subsequent respiration cycles and the movement signal (from movement sensor 302) has not indicated movement of the patient the pacing processor 201 switches to an extended reduced activity respiration mode (or extended reduced mode), block 309. At the same time the new SD, MV and corresponding expected respiration cycles are calculated as explained above based on all or a number of the last detected subsequent respiration cycles.

During the extended reduced mode the system behaves in the same way as describe above with reference to the initial reduced mode. There are just three differences: (i) the system may be configured to count another (a higher) number of respiration cycles, e.g. 30, before it is allowed to switch to the prolonged reduced mode; (ii) the respiration sensor is active only during each $n^{th}$ expected respiration cycle, where n is a natural number, e.g. 3. In contrast, the movement sensor may be active all time and, therefore, also may contribute to the counting of the number of respiration cycles. And again the new SD, MV and corresponding expected respiration cycles are calculated as explained above based on all or a number of the last detected subsequent respiration cycles when the system switches to the prolonged reduced mode; (iii) if none of the sensors encounter a inspiratory event that is counted in the respiration counter, block 311, the pacing sensor 201 may switch back to reduced respiration mode, block 305, and the respiration sensor recommence measurement of the respiration signal at and around each expected respiration cycle.

After the movement signal has remained unchanged for a prolonged inactive period, for example, thirty to fifty breaths without movement (more than 5-30 min), block 312, the pacing processor 201 enters a prolonged inactive respiration mode, block 313. In that mode, the pacing processor 201 measures the respiration signal much less frequently during a limited respiration sampling period that occurs briefly at the beginning of the mode, for example, one to three breaths, as shown in FIG. 4. Between those 10-30 breaths there is no recording phase of the respiration sensor signal, and the movement sensor derived respiratory signal is calculated for every inspiratory event. These will be correlated with the expected inspiratory events from the RSS. For all following breathing stimuli, the expected breath stimulus is taken. The prolonged inactive mode is useful in longer stable conditions to save a great deal of energy—for example, during sleep—where no patient movement is observed and a constant respiratory rate is expected. Again, once the movement signal eventually does change again, block 314, then the operation mode of the pacing processor 201 shifts back to the active respiration mode, block 301. If no respiration pacing trigger can be calculated from the respiration sensor signal, the movement sensor derived respiratory signal will be looked at. If none of those sensors encounter an inspiratory event that is counted in the respiration counter, block 315, the pacing sensor 201 may switch back to the initial reduced activity respiration mode, block 305.

The specific movement sensor in such arrangements may be a small package that can easily be integrated into the housing of the pacing processor 201;

With respect to the specific implementation of a respiration sensor 202, it will be appreciated that during the inspiration phase of breathing, the various respiratory muscles—such as the diaphragm, intercostal externi, and the parasternal part of the intercostal interni muscles—are always active. With every breathing cycle, during inspiration those muscles are involuntarily active and contract. In particular, the parasternal muscle (also called the intercartilaginous muscle or the parasternal part of the intercostal interni muscle) elevates the ribs during inspiration. Thus, some specific embodiments of the present invention use the contraction of the parasternal muscle, specifically via a parasternal respiration sensor 202 implemented as, for example, an electromyogram (EMG) sensor, pressure sensor.

The parasternal muscle has a medial to dorsal gradient of activity and muscle mass as well as a cranial caudal gradient, which means that the parasternal muscle becomes smaller from the sternum to the base of the rib. A parasternal respiration sensor 202 can be inserted into the parasternal muscle in a rib interspace in the thorax near the sternum and the pacing processor (see FIG. 2), preferably in the 2nd or $3^{rd}$ interspace, and a reliable respiration signal from the parasternal muscle is thereby available. The 2nd or 3rd interspace provides the thickest proportion of the muscle (around 6-10 mm) in which to secure the respiration sensor 202, and also provides the smallest part of the pectoralis muscle where there is the least overshadowing effect to be expected. In addition, this location is spatially close to the pacing processor 201 and the surgical placement of the respiration sensor 202 into the parasternal muscle is minimally invasive and surgically uncomplicated.

A parasternal respiration sensor in combination with together with a movement sensor also can avoid misstimulation during active rotation and bending of the thorax. The parasternal muscle is known to be active during rotation and bending of the thorax, and with the help of the movement sensor these specific bendings and rotations can be measured and mis-stimulation avoided.

A respiration implant system with both a respiration sensor and a movement sensor may also be usefully adapted to provide an effort-based respiration pacing signal. That is, a three-axis accelerometer movement sensor can identify not only whether or not an implanted patient is in motion, but can also be used to determine if the patient is sitting, standing, or lying down, and if moving, how fast. And a parasternal respiration sensor as described above also correlates to the effort in breathing. In addition, a gyroscope sensor measuring two or more axes can be provided to detect angular changes due to body rotation. If there is ipsilateral movement (same side as the respiration sensor), then the parasternal muscle is active and the EMG signal needs to be ignored during that motion. But if the gyroscope sensor indicates contralateral movement, no EMG activation will be seen.

The combination of these sensor inputs can be used to determine the position and respiratory effort of the patient. The pacing processor can then use this to correspondingly control the pulse rate, pulse width, and pulse amplitude of the respiration pacing signal. This better supports the patient's needs during active exercise and also helps save precious battery power during reduced activity (e.g., sleeping, sitting, etc.).

Besides for treatment of impaired laryngeal structures via stimulation of the posterior cricoarytenoid muscle, embodiments of the present invention also may be useful for treatment of sleep apnea. During sleep for those afflicted with this disease, apnea events occur where the airway is blocked and no air comes in or goes out. The respiratory effort increases when the airway starts to block up and increases greatly if the airway becomes blocked. In that situation, all respiratory muscles including the parasternal muscle show increased innervation in an effort to restart the airflow. This increased neural activity can be recorded as an increase in respiratory effort in the parasternal muscle sensor, either based on the pressure difference between inspiration and expiration (maximum to minimum pressure) for each breath or the increased EMG activity can be detected. And in such an apnea treatment system, an acceleration-based movement sensor as discussed above can be useful to automatically detect when a person is lying down and sleeping in order to start measuring the respiration signal from the respiration sensor to detect an apnea event.

So if the respiratory effort change exceeds a certain threshold level and has been increased over recent breaths, then an apnea event is detected. Then the pacing processor can use the respiration signal from the parasternal respiration sensor to determine a given specific point during the respiratory cycle, for example, the start or end of inspiration or expiration. The pacing processor then generates a respiratory-synchronized stimulus signal to the respiratory muscles (e.g., the hypoglossal nerve) until an improvement is detected in the respiration signal that indicates that the apnea event has been resolved. In some embodiments, triggered respiratory stimulation may commence as soon as the respiratory effort increases slightly in order to prevent the apnea.

Embodiments of the invention may be implemented in part in any conventional computer programming language such as VHDL, SystemC, Verilog, ASM, etc. Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of developing a respiration pacing signal in an implanted patient with impaired breathing, the method comprising:
    detecting respiration activity in the implanted patient and developing a corresponding respiration signal;
    detecting movement of the implanted patient and developing a corresponding movement signal;
    using a pacing processor to follow a series of computer instructions fixed on a non-transitory computer readable medium to receive the respiration signal and the movement signal and generate a respiration pacing signal synchronized with the detected respiration activity; and
    delivering the respiration pacing signal from the pacing processor with a stimulating electrode to respiration neural tissue of the implanted patient to promote breathing of the implanted patient;
    wherein using the pacing processor includes using a plurality of respiration sensing modes that reflect activity of the movement signal over time to optimize system power consumption over time,
    wherein the plurality of respiration sensing modes includes:
        i. an active respiration mode when the movement signal is either actively changing or remains unchanged for a period less than a reduced activity period, wherein the respiration signal is measured continuously, and
        ii. a plurality of reduced activity respiration modes when the movement signal remains unchanged for the reduced activity period, wherein the respiration signal is measured only during a limited respiration sampling period.

2. The method according to claim 1, wherein the plurality of reduced activity respiration modes includes an initial reduced activity respiration mode during which the movement signal has remained unchanged for an initial reduced activity period and in which the respiration signal is measured only during a limited respiration sampling period occurring around each expected breathing phase.

3. The method according to claim 1, wherein the plurality of reduced activity respiration modes includes an extended reduced activity respiration mode during which the movement signal has remained unchanged for an extended reduced activity period and in which the respiration signal is measured only during a limited respiration sampling period occurring between each third to tenth breath.

4. The method according to claim 1, wherein the plurality of reduced activity respiration modes includes a prolonged inactive respiration mode during which the movement signal has remained unchanged for a prolonged inactive period and in which the respiration signal is measured only once during a limited respiration sampling period occurring at the beginning of the prolonged inactive respiration mode.

5. The method according to claim 1, wherein the movement signal is filtered in the plurality of reduced activity respiration modes to develop a respiratory signal representing rib cage movement.

6. The method according to claim 1, wherein detecting the respiration signal includes detecting an onset of inspiratory phase in the implanted patient.

7. The method according to claim 1, wherein detecting the respiration signal includes using a three-axis accelerometer.

8. The method according to claim 1, wherein detecting the respiration signal includes using an electromyographic sensor implanted in the parasternal muscle of the implanted patient.

9. The method according to claim 1, wherein detecting the respiration signal includes using an intramuscular pressure sensor implanted in the parasternal muscle of the implanted patient.

10. The method according to claim 1, wherein the stimulating electrode delivers the respiration pacing signal to the posterior cricoarytenoid muscle in the larynx.

11. The method according to claim 1, wherein t the stimulating electrode delivers the respiration pacing signal to the hypoglossal nerve or the internal superior laryngeal nerve (iSLN).

* * * * *

UNITED STATES PATENT AND TRADEMARK OFFICE
CERTIFICATE OF CORRECTION

PATENT NO. : 9,656,082 B2
APPLICATION NO. : 15/340007
DATED : May 23, 2017
INVENTOR(S) : Christian Denk It is certified that error appears in the above-identified patent and that said Letters Patent is hereby corrected as shown below:

In the Claims

In Column 10, Line 54:
Delete "t" after "wherein"

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*